United States Patent [19]

Giuliani et al.

[11] Patent Number: 5,784,742
[45] Date of Patent: Jul. 28, 1998

[54] TOOTHBRUSH WITH ADAPTIVE LOAD SENSOR

[75] Inventors: David Giuliani, Mercer Island; Ryan W. McMahon; James Christopher McInnes, both of Seattle, all of Wash.

[73] Assignee: Optiva Corporation, Bellevue, Wash.

[21] Appl. No.: 494,322

[22] Filed: Jun. 23, 1995

[51] Int. Cl.⁶ .................................................. A46B 13/02
[52] U.S. Cl. ........................ 15/22.1; 15/167.1; 433/216; 340/665; 340/679
[58] Field of Search .................... 15/105, 22.1, 22.2, 15/22.4, 23, 24, 28, 167.1, 49.1; 340/679, 540, 665; 433/118, 119, 216

[56] References Cited

U.S. PATENT DOCUMENTS

| | | | |
|---|---|---|---|
| 4,253,212 | 3/1981 | Fujita | 15/167.1 |
| 4,450,599 | 5/1984 | Scheller et al. | 15/22.1 |
| 4,476,604 | 10/1984 | White et al. | 15/167.1 |
| 4,679,271 | 7/1987 | Field et al. | 15/49 R |
| 4,680,825 | 7/1987 | White et al. | 15/167.1 |
| 4,698,869 | 10/1987 | Mierau et al. | 15/22.1 |
| 4,716,614 | 1/1988 | Jones et al. | 15/167.1 |
| 4,744,124 | 5/1988 | Wang et al. | 15/167.1 |
| 4,766,432 | 8/1988 | Field et al. | 340/679 |
| 5,146,645 | 9/1992 | Dirksing | 15/167.1 |
| 5,214,819 | 6/1993 | Kirchner | 15/22.1 |
| 5,263,218 | 11/1993 | Giuliani et al. | 15/22.1 |
| 5,331,707 | 7/1994 | Irizarry | 15/167.1 |
| 5,355,544 | 10/1994 | Dirksing | 15/167.1 |
| 5,378,153 | 1/1995 | Giuliani et al. | 15/22.1 |
| 5,493,747 | 2/1996 | Inakagata et al. | 15/22.1 |
| 5,561,881 | 10/1996 | Klinger et al. | 15/22.1 |

FOREIGN PATENT DOCUMENTS

| | | |
|---|---|---|
| 481553 | 4/1992 | European Pat. Off. . |
| 3724476 | 7/1987 | Germany . |
| 4319015 | 6/1993 | Germany . |
| 3191905 | 8/1991 | Japan . |
| 237014 | 9/1993 | Japan ............... 15/22.1 |
| 329024 | 12/1993 | Japan ............... 15/22.1 |
| 609238 | 3/1976 | Switzerland . |
| 9202159 | 2/1992 | WIPO . |
| 9210979 | 7/1992 | WIPO . |
| 9213499 | 8/1992 | WIPO . |
| 9220256 | 11/1992 | WIPO . |
| 9405229 | 3/1994 | WIPO . |
| 9409675 | 5/1994 | WIPO . |

OTHER PUBLICATIONS

Translation of Swiss 609,238 Bugnion, S.A., Feb. 1979. All translated pages (9) plus cover page (1) 10 total pages.

Primary Examiner—Gary K. Graham
Attorney, Agent, or Firm—Jensen & Puntigam, P.S.

[57] ABSTRACT

An electric toothbrush (10) with an adaptive load sensor (12) is disclosed. The toothbrush of this invention includes a brushhead (16) that is vibrated by a drive assembly (18). The load sensor monitors the current drawn by the drive assembly to determine the mechanical load to which the toothbrush is exposed. The load sensor assembly produces an adaptive threshold signal that represents the instantaneous maximum pressure load. If the sensed load voltage exceeds the adaptive threshold signal, the load sensor assembly deenergizes the drive assembly and generates an alarm signal so as to give the user a warning that the toothbrush has been excessively loaded.

28 Claims, 7 Drawing Sheets

TOOTHBRUSH WITH ADAPTIVE LOAD SENSOR

TECHNICAL FIELD

This invention relates generally to an electric toothbrush and more particularly, to an electric toothbrush with an adaptive load sensor for preventing excessive loading of the brush against the mouth tissues and the teeth.

BACKGROUND OF THE INVENTION

Electric toothbrushes have proven to be useful home appliances for fostering proper oral hygiene. A typical electric toothbrush includes a base which functions as a handle and a stem that extends outwardly from the base. A set of bristles is secured to the free end of the stem to form a brushhead. A drive unit located inside the base is coupled to the stem. When the drive unit is activated, it causes the stem and brushhead to move in an oscillatory pattern. When an individual places the brushhead in his/her mouth and against the teeth, the oscillatory movement of the bristles both scrubs contaminants off the tooth enamel and massages the adjacent soft gum tissue, referred to as the gingiva. This massaging of the gingiva serves to strengthen the tissue.

Recently, electric toothbrushes that vibrate at sonic frequencies, approximately 200 to 500 Hz, have been developed. The brushhead vibrations produced by these toothbrushes induce the saliva, water and other fluids in the individual's mouth to vibrate. These vibrating fluids are quite useful, since they serve to further clean the exposed tooth surfaces in the individual's mouth and also to clean those tooth surfaces that are difficult to reach directly by the bristles.

One limitation associated with the utility of all toothbrushes, including electric toothbrushes, is that care must be taken by the individual to ensure that he/she does not use excessive pressure when applying the bristles to the teeth. Excessive pressure can result in tissue abrasion and damage. Correct pressure, on the other hand, can enhance clinical results. Further, when an individual uses excessive pressure in applying the toothbrush to the teeth, the pressure tends to cause the vibrations of the brushhead to appreciably slow and, in some cases, come to a complete stop. In many cases, the slowing of the vibratory motion of the brushhead essentially causes all the advantages otherwise gained by the use of the toothbrush to be lost. This is especially true in the case of sonic vibrating toothbrushes. When excessive pressure loading causes these brushheads to slow and vibrate at smaller amplitudes, the bristles no longer can induce proper vibration of the adjacent oral fluids. Consequently, advantages normally gained by using this type of toothbrush are substantially lost.

There have been attempts to provide pressure sensors to warn an individual that he/she is using excessive force with an electric toothbrush. Typically, these sensors include an electromechanical transducer that is connected to the stem of the toothbrush. The transducer, in response to the pressure loading on the stem, generates signals which affect another component of the toothbrush. For example, one pressure sensor includes a normally open switch that closes upon the bending of the stem under pressure. Still other toothbrushes include piezoelectric transducers that generate a particular set of signals in response to the pressure loads applied thereto. Once these sensors detect a pressure overload condition, they either actuate an alarm and/or deactivate the toothbrush drive unit.

While the various pressure sensors that to date have been used to provide some sort of pressure monitoring have proved useful, they are not without their own limitations and complications. Many of the pressure sensors currently in use include a mechanical member that is attached to the stem or drive unit in order to monitor pressure applied to the teeth and/or tissues. The addition of these mechanical components to a toothbrush adds to its complexity and cost. Moreover, some of the additional components occupy so much space that it has proved difficult, if not commercially impractical, to install them on toothbrushes. Further, the friction resulting from the contact of these sensors against the other components of the toothbrush induces a needless drain of the energy needed to actuate the toothbrush. In the case of toothbrushes with rechargeable batteries, this drain could cause the batteries to discharge at a rate that substantially increases the frequency of recharging.

The operating conditions of many toothbrush pressure sensors are typically established at the time of manufacture. A disadvantage of such an arrangement is that for many electric toothbrushes, component wear or dentifrice buildup will change the pressure required to activate the warning alarm and/or deactivate the toothbrush drive unit. Also, different brushheads will often produce different triggering. This is of course undesirable. The available pressure sensors with their preset, fixed threshold signal levels thus are of relatively limited usefulness for electric toothbrushes.

In addition, the pressure sensing methods in the prior art were developed for conventional mechanical toothbrushes. Sonic vibrating toothbrushes operate at significantly lower applied pressures than conventional brushes. For example, the brush described in U.S. Pat. No. 5,263,218 has been shown to use loading forces of typically 60 grams, which is about 25% of that used in manual brushing, and less than half of that of a typical commercial electric toothbrush. The lower pressures typically used by sonic toothbrushes exacerbate the limitations of mechanical overload sensors.

DISCLOSURE OF THE INVENTION

Accordingly, the present invention is directed to an electric toothbrush assembly with an adaptive load sensor for monitoring the load imposed on the brushhead. The toothbrush assembly of this invention includes a drive assembly that is actuated by a power source; a brushhead with a set of bristles attached to the drive assembly that vibrates in response to the energization of the drive assembly by electrical drive signals; a load sensor coupled to the drive assembly for monitoring the electrical drive signals; and an alarm unit coupled to the load sensor for generating an appropriate response whenever the sensor detects an excess loading condition.

In one embodiment of the invention, a digital microprocessor is employed to analyze the variations in loading. The processor is constructed so as to constantly update the no-load signals being produced. The microprocessor produces an adaptive threshold signal that compensates for changes in the operating state of the toothbrush as it is being used throughout the individual brushing cycle and throughout the lifetime of the toothbrush.

BRIEF DESCRIPTION OF THE DRAWINGS

The above and further features of this invention will become clear from a review of the following description and by reference to the following drawings in which.

Best Mode for Carrying Out the Invention

Figure 1:
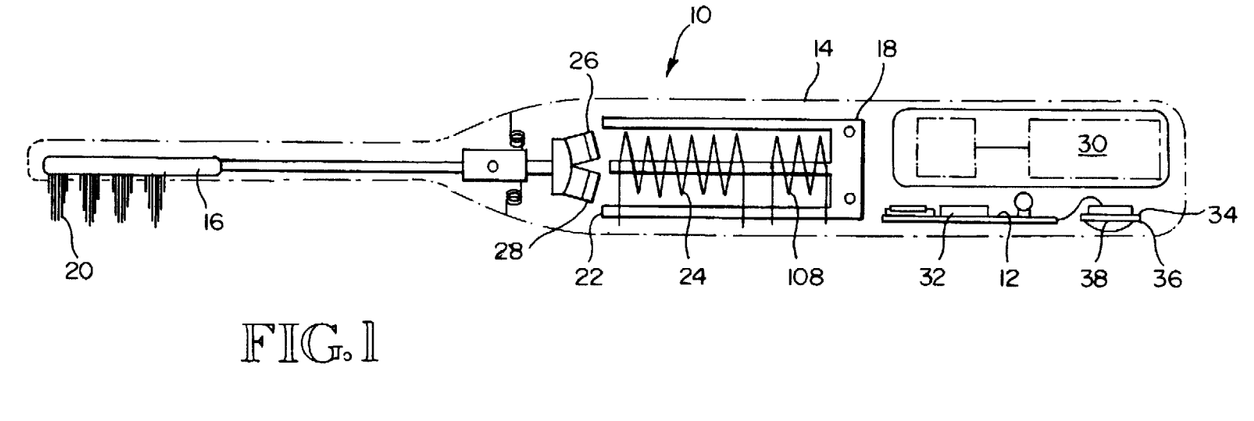
FIG. 1 illustrates an electric toothbrush incorporating the adaptive load sensor assembly of this invention.

FIG. 1 depicts an electric toothbrush 10 that incorporates the adaptive load sensor assembly 12 of this invention. The toothbrush 10 includes an outer case 14 from which a brushhead 16 extends. A set of bristles 20 is attached to the free end of the brushhead 16. Located inside the case 14 is an electrically powered drive assembly 18. The drive assembly 18 is coupled to the brushhead 16 so that when the drive assembly is actuated, the brushhead 16 and bristles 20 vibrate in an oscillatory pattern.

In the depicted version of the invention, driving assembly 18 includes an electromagnet 22 that has an E-shaped core. A coil 24 is wrapped around the center leg of the core 22. Integral with the brushhead 16 are a set of magnets 26 and 28. Electromagnet 22 is energized by a rechargeable battery 30 located in the toothbrush case 14. A control circuit 32 selectively controls the application of voltages across coil 24 so as to induce oscillating magnetic fields of alternating and opposite polarity in the vicinity of the brushhead magnets 26 and 28. The periodic establishment and collapsing of the magnetic fields causes magnets 26 and 28 and the other components of the brushhead 16 to oscillate. In one particular toothbrush, the brushhead is forced to oscillate at a frequency in the range of 200–500 Hz and, more particularly, approximately 260 Hz. In this embodiment, the brushhead has a bristle tip velocity of at least 1.5 meters per second and a bristle tip amplitude in the range of 1 millimeter to 6 millimeters. A more detailed description of the construction of toothbrush 10 can be found in U.S. Pat. Nos. 5,263,218 and 5,378,153, which are assigned to the assignee of this application and are incorporated herein by reference.

Load sensor assembly 12 is incorporated into drive circuit 32. The load sensor assembly 12 includes a small alarm 34 that is located in the lower portion of toothbrush case 14. The alarm could be audible or a drive interrupt, or a small increase in frequency (double) for a brief time, which produces a difference in sound. In one version of the invention, alarm 34 includes a piezoelectric element 36 mounted to a flexible diaphragm 38. When piezoelectric element 36 is actuated, it causes sufficient vibration in the diaphragm 38 so as to result in an audible alarm.

As will be discussed hereinafter, whenever the load sensor assembly 12 detects excessive loading of brushhead 16 in the embodiment shown, the load sensor assembly causes control circuit 32 to deenergize drive assembly 18. Simultaneously with the deactivation of drive assembly 18, load assembly 12 activates alarm 34 so as to cause the emission of an audible warning that the brushhead 16 has been excessively loaded.

Figures 2, 3:
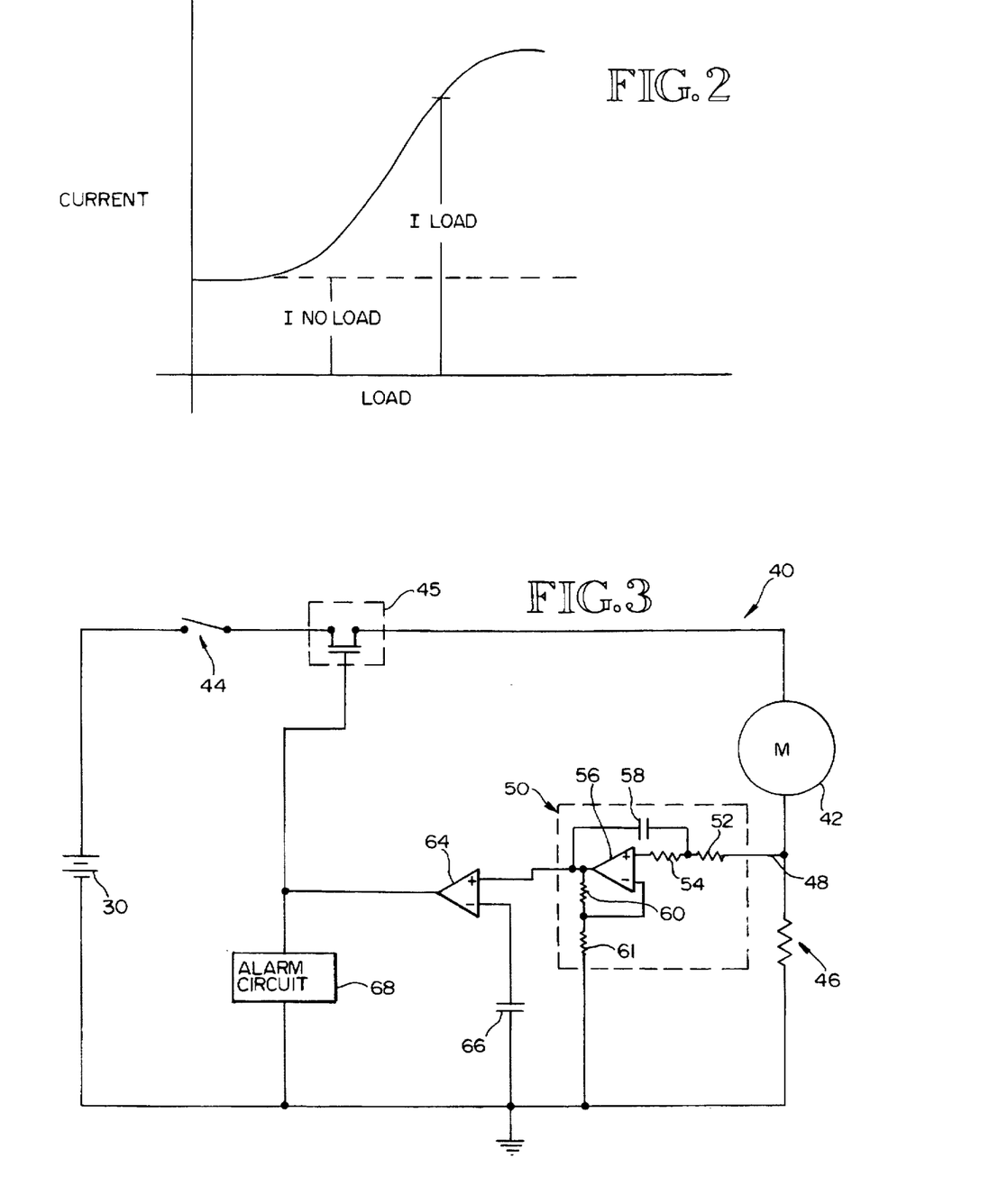
FIG. 2 graphically depicts how the current drawn by the toothbrush drive assembly can serve as an indicia of the load being applied on an electric toothbrush.
FIG. 3 is a schematic diagram of an analog version of the load sensor assembly of the present invention.

Load sensor assembly 12 of the present invention monitors the loading of brushhead 16 by monitoring the current drawn by drive assembly 18. As depicted in FIG. 2, when there is no load placed on brushhead 16, drive assembly 18 draws a minimal amount of current $I_{NOLOAD}$ in order to vibrate the brushhead. When a force is applied to the brushhead 16, as is the situation when it is applied to the teeth or gums, the current required to vibrate the brushhead 16 increases. As the load imposed on the brushhead 16 increases, the current drawn by drive assembly 18 undergoes a like increase, and is referred to as load current $I_{LOAD}$.

FIG. 3 is a schematic diagram of an analog circuit 40 that can be employed as the load sensor assembly 12 of this invention. In circuit 40, the drive assembly that actuates brushhead 16 is depicted diagrammatically as motor 42. Motor 42 is energized by a battery 30. The actuation of motor 42 is controlled by a manually set switch 44. A sensor resistor 46 is connected between motor 42 and the circuit ground. Since the current through resistor 46 is equal to the current drawn by motor 42, and the voltage across resistor 46 is proportional to the current through the resistor, the load imposed on the motor is measured as the voltage across the resistor.

In circuit 40, the voltage across sensor resistor 46, the load signal, is measured through a lead 48 which is connected at one end to the junction between motor 42 and resistor 46. The voltage across resistor 46 is applied through lead 48 to a low pass filter shown generally at 50. In this version of the invention, low pass filter 50 includes two series-connected resistors 52 and 54, respectively, which apply the voltage across resistor 46 to the positive input of an operational amplifier 56. A capacitor 58 is connected between the junction of resistors 52 and 54 and the output of operational amplifier 56. The output of operational amplifier 56 is also tied to ground through two series-connected resistors 60 and 61. The negative input of operational amplifier 56 is tied to the junction between resistors 60 and 61.

Filter 50 is designed to filter out high frequency voltage spikes that may appear across resistor 46 as a result of any temporary loading of the toothbrush. In some preferred versions of the invention, filter 50 is designed to filter out voltage spikes indicative of a temporary high loading of motor 42 that are less than 500 milliseconds in duration. In more preferred embodiments of the invention, filter 50 is designed to filter out voltage spikes of a duration of 200 milliseconds or less.

The filtered load signal is applied to the positive input of a comparator 64. A reference voltage, the threshold signal, is applied to the negative input of the comparator. In the illustrated version of the invention, a separate power supply 66 is used to supply the threshold signal to comparator 64. When the filtered load signal is less than the reference voltage, the comparator 64 output is at zero volts. Whenever the filtered load signal exceeds the threshold signal level, comparator 64 goes into positive saturation and generates an output or alarm signal.

The preferred embodiment of a sonic toothbrush involves a threshold setting corresponding to a load of approximately 90–150 grams of force when the bristles are loaded onto the teeth. This results in an overload indication when the sustained applied force exceeds approximately 50% to 150% over the typical loading, which is about 60 grams.

The alarm signal generated by the comparator 64 is applied to an electronically controlled switch 45 so as to deenergize toothbrush motor 42 and prevent the further overloading of the components forming the toothbrush 10.

As depicted in this version of the invention, switch 45 is in the form of a normally closed MOSFET, though it can of course take other forms. The alarm signal generated by comparator 64 is also applied to an alarm circuit 68 so as to cause the actuation of the alarm 34 in order to provide the individual an audible notice that the toothbrush 10 has been subjected to excessive loading that should be reduced.

Load sensor assembly 12 of this invention provides a convenient means for both deactivating the toothbrush drive assembly 18 when the load (pressure) reaches levels which may be damaging to tissue, and for providing notice that the toothbrush has been subjected to such loading. Rather than completely deactivating the drive assembly, it is possible to only temporarily interrupt the drive, or a change in the drive signal could be used, such as pulses or a doubling of the frequency, which would act like a null for bristle movement. Load sensor assembly 12 monitors the load by monitoring the current required to actuate the toothbrush drive assembly 18. Consequently, this invention does not require any separate mechanical load-sensing components that both occupy space and that can appreciably detract from the overall operational efficiency of toothbrush 10.

Another advantage gained by the elimination of mechanical sensing components is that there is no risk that, over time, such components can be gummed up or otherwise restricted by water, toothpaste or other contaminants and, as a result, malfunction. Thus, load sensor assembly 12 of this invention provides a convenient means of monitoring the loading of an electric toothbrush 10 that can readily be installed in the toothbrush without significantly adding to the overall complexity of the toothbrush or significantly interfering with its operation.

Figure 4:
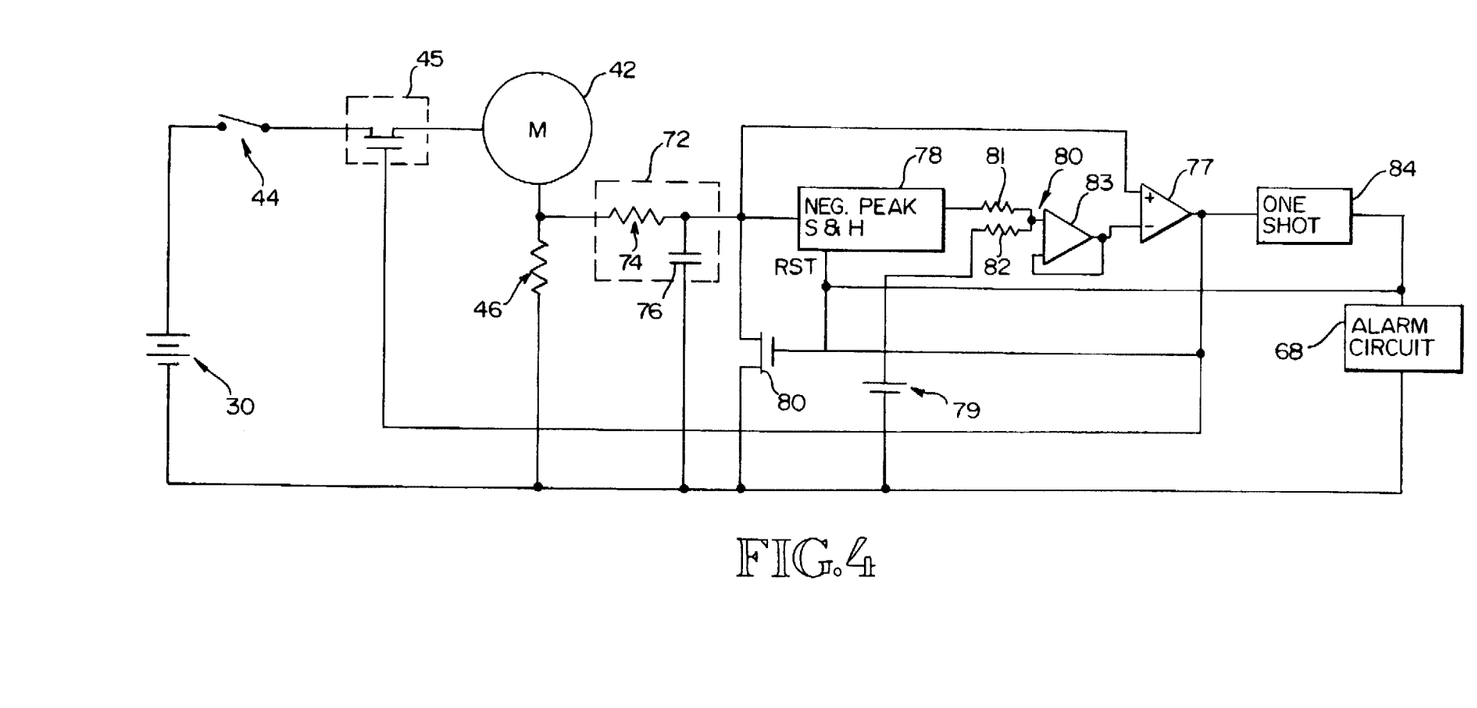
FIG. 4 is a schematic diagram of an alternative analog circuit for the load sensor assembly of the present invention.

An alternative load sensor assembly of the present invention is depicted by the schematic diagram of FIG. 4. In this diagram, motor 42, battery 30, manual switch 44, normally closed switch 45 and sensor resistor 46 perform the same general functions as they performed with respect to the load sensor assembly of FIG. 3. In this version of the invention, the load signal developed across sensor resistor 46 is filtered by a low-pass filter 72. Filter 72 includes a resistor 74 connected at one end to the junction between motor 42 and resistor 46. A capacitor 76 connected between the end of resistor 74 distal from the motor and ground completes filter 72.

The filtered load signal from filter 72 is applied to a negative peak sample-and-hold circuit 78. The stored negative peak load signal and a reference voltage from a dedicated voltage source 79 are applied to a summing circuit 80. In the depicted version of the invention, summing circuit 80 includes two resistors 81 and 82 through which the stored negative peak load signal and the reference signal 79 are respectively applied. The signals through resistors 81 and 82 are applied to the positive input of an operational amplifier 83. The negative input of amplifier 83 is tied to the amplifier output so as to cause the amplifier to function as a unity gain buffer amplifier. The output signal produced by amplifier 83 is referred to as an adaptive threshold signal. This signal initially is relatively high and can decrease with the decrease of the filtered load signal.

The filtered load signal and the adaptive threshold signal are, respectively, applied to the positive and negative inputs of a comparator 77. Whenever the filtered load signal is greater than the adaptive threshold signal, that condition is recognized as indicating that the toothbrush 10 is being subjected to excess loading. In this situation, comparator 77 emits an alarm signal. The alarm signal generated by comparator 77 is applied to switch 45 to bias the switch open in order to cause the deenergization of toothbrush motor 42. The comparator 77 alarm signal is also applied to a one-shot multivibrator 84. Multivibrator 84 upon receipt of this signal generates an alarm signal of fixed time period. The output signal from multivibrator 84 is applied to alarm circuit 68 to cause the generation of an audible warning signal of fixed duration.

The output signal from comparator 77 is also applied to a normally open MOSFET 88 that is tied across capacitor 76. When comparator 77 generates an output signal, MOSFET 88 is biased into conduction so as to discharge capacitor 76 and reset filter 72. The output of multivibrator 84 is further applied to sample-and-hold circuit 78 as a reset signal. The adaptive level threshold is reset during each two-minute use of the apparatus. A no-load condition is established during use. A fixed value is then added to the no-load value to establish the threshold. Sensitivity of the brush thus increases after the toothbrush is turned on. The threshold will vary from head to head or as a result of changes due to component wear. Thus, the threshold "adapts" to the changing conditions.

The load sensor assembly of FIG. 4 performs the same basic load monitoring described with respect to the sensor assembly of FIG. 3. In the FIG. 4 version of the invention, however, the filtered load signal is compared to an adaptive threshold signal. In this particular embodiment, the adaptive threshold signal is equal to the sum of the fixed reference voltage and the negative peak load signal stored in the sample-and-hold circuit 78. Thus, this feature of the invention compensates for the fact that, during a brushing cycle, as the toothpaste and water inside an individual's mouth mix and become less viscous, the no-load current drawn by the drive assembly 18 decreases. An advantage of being able to compensate for the decreasing no-load current is that it eliminates the need to provide a fixed threshold signal which does not accurately indicate the conditions when the load sensor assembly should interrupt the toothbrush drive assembly or momentarily change the drive frequency.

The adaptive-type generation of the threshold signal similarly compensates for changes in the drive assembly no load current that occur as a result of the wear of the components of the toothbrush 10 throughout the lifetime of the toothbrush, as well as compensating for differences in replacement heads.

Still another feature of the assembly of FIG. 4 is that when the filtered load signal exceeds the adaptive threshold signal, MOSFET 88 is biased into conduction so as to force the discharge of capacitor 76. The discharging of capacitor 76 resets filter 72. This prevents the continued application of relatively high voltages to comparator 77, which, in turn, can cause the continued generation of the alarm signal. This arrangement prevents superfluous additional warning signals from being asserted. Moreover, the audible signal is only generated for the period equal to the duration of the signal asserted by the one-shot multivibrator 84. Collectively, these features prevent the toothbrush 10 from generating either unduly repetitive or excessively long alarm signals, either of which can quickly become irritating.

Figure 5:
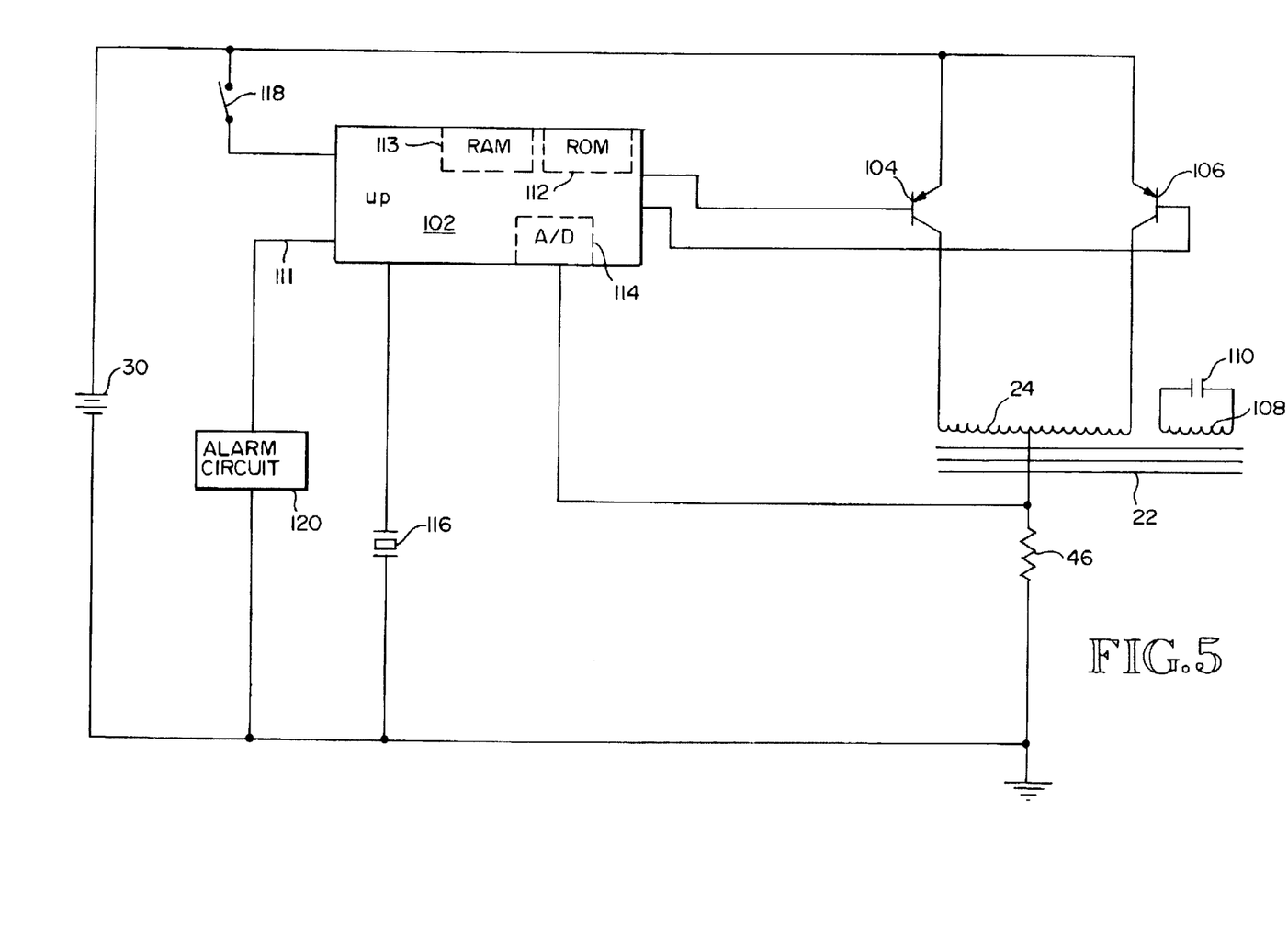
FIG. 5 is a schematic diagram showing a digital circuit that can be used to both energize an electric toothbrush and that incorporates the load sensing assembly of this invention.

FIG. 5 is a schematic diagram of a load sensor assembly embodiment of this invention that includes a microprocessor 102 that both controls the energization of the drive assembly and monitors the load placed on brushhead 16. As seen in this figure, the opposed ends of transformer winding 24 are disposed around the center leg of E-core electromagnet 22 and are each attached to the collectors of separate PNP transistors 104 and 106. The emitters of transistors 104 and 106 are tied to the positive terminal of battery 30 that energizes both winding 24 and power microprocessor 102 ($V^+$ microprocessor connection not shown). The center tap of winding 24 is tied to ground through sensor resistor 46.

Drive assembly 12 further includes a tank circuit comprising a secondary transformer winding 108 that is disposed around the center leg of the electromagnet 22 and a capacitor 110 that is connected across winding 108. Coil 108 and capacitor 110 are selected to have a resonant frequency similar to that of the drive signal applied to winding 22. In one preferred embodiment of the invention, winding 24 consists of approximately 90 turns of No. 26 wire and sensor resistor 46 has a resistance of approximately 0.1 ohms. In this version of the invention, winding 108 consists of approximately 3000 turns of No. 33 wire and capacitor 110 has a capacitance of approximately 0.82 microfarads. The tank circuit formed by winding 108 and capacitor 110 minimizes the dissipation of the power generated across winding 24.

Microprocessor 102 is capable of selectively biasing transistors 104 and 106 into conduction so as to cause an alternating current to flow through winding 24. The voltage developed across resistor 46, the load signal, is analyzed to determine the load to which the brushhead 16 is subjected and to provide a load-based regulation of the energization of the toothbrush. One microprocessor capable of preforming these functions is a four-bit microprocessor MC68HC705P9 manufactured by Motorola Inc. of Schaumberg, Ill. Microprocessor 102 has an internal read-only memory 112 in which the instructions required to control the operation of the toothbrush 10 are stored and a RAM memory 113 in which the data being processed by the microprocessor is stored.

Microprocessor 102 further includes an internal analog-to-digital signal converter 114 capable of converting the analog load signal developed across sensor resistor 46 into an 8-bit digital signal. A clock signal controlling the operation of microprocessor 102 is supplied by a small clock unit represented by crystal 116. In some preferred embodiments of the invention, microprocessor 102 may operate at a clock rate of between 100 kHz and 16 MHz and, in still more preferred versions of the invention, at a clock rate between 1 MHz and 7 MHz.

A normally open, manually actuated switch 118 is tied between the positive terminal of battery 30 and input 109 of the microprocessor 102. Switch 118 when closed applies a voltage to an input pin of microprocessor 102 that functions as a UNIT-ON signal that indicates use of the toothbrush is desired. The bases of transistors 104 and 106 are tied to separate output pins of microprocessor 102. Once the UNIT-ON signal is asserted, microprocessor 102 energizes drive assembly 18 (FIG. 1) by applying voltages to transistors 104 and 106 so that they are alternately biased into allowing current to flow therethrough. The alternating current flow through transistors 104 and 106 causes an oscillating magnetic field to develop around winding 24. This magnetic field in turn induces oscillating opposed polarity magnetic fields to develop in the vicinity of the opposed legs of the core 22. The magnetic fields around the opposite legs of core 22 in turn cause brushhead 16 to rapidly vibrate back and forth so as to induce a like motion of the bristles necessary for the desired scrubbing effect.

An ALARM signal is asserted by microprocessor 102 at a third output pin 111. This signal is applied to an alarm circuit 120. In the event microprocessor 102 detects a load signal from across sensor resistor 46 that indicates that the brushhead 16 is subjected to excessive loading, microprocessor 102 alters the assertion of the biasing signals necessary to force transistors 104 and 106 into conduction so as to produce a frequency doubling. Alternatively, the biasing signals could be altered to produce a "pulsing" bristle effect. Simultaneously with the change in the transistor biasing signals, microprocessor 102 asserts the ALARM signal. Receipt of the ALARM signal by the alarm circuit 120 causes the actuation of the alarm so that the individual using the toothbrush receives an indication (could be tactile or audible) that the brushhead has been subjected to excessive loading.

An alternative overload sensor is a lamp which is illuminated when a sustained overload condition is sensed. An LED (light emitting diode) can be used, placed where the user can conveniently see it; for example, behind the switch cover, when the cover is made from a translucent material. However, a visual indication of overload is limited to those viewing angles which can be seen by the user, typically in the mirror. In an improved configuration, the visual indicator is located in a charger base portion of the apparatus. When the charger base is placed on the counter in front of the user, he or she can look approximately straight ahead and easily notice when the overload visual indicator is illuminated.

Figure 8:
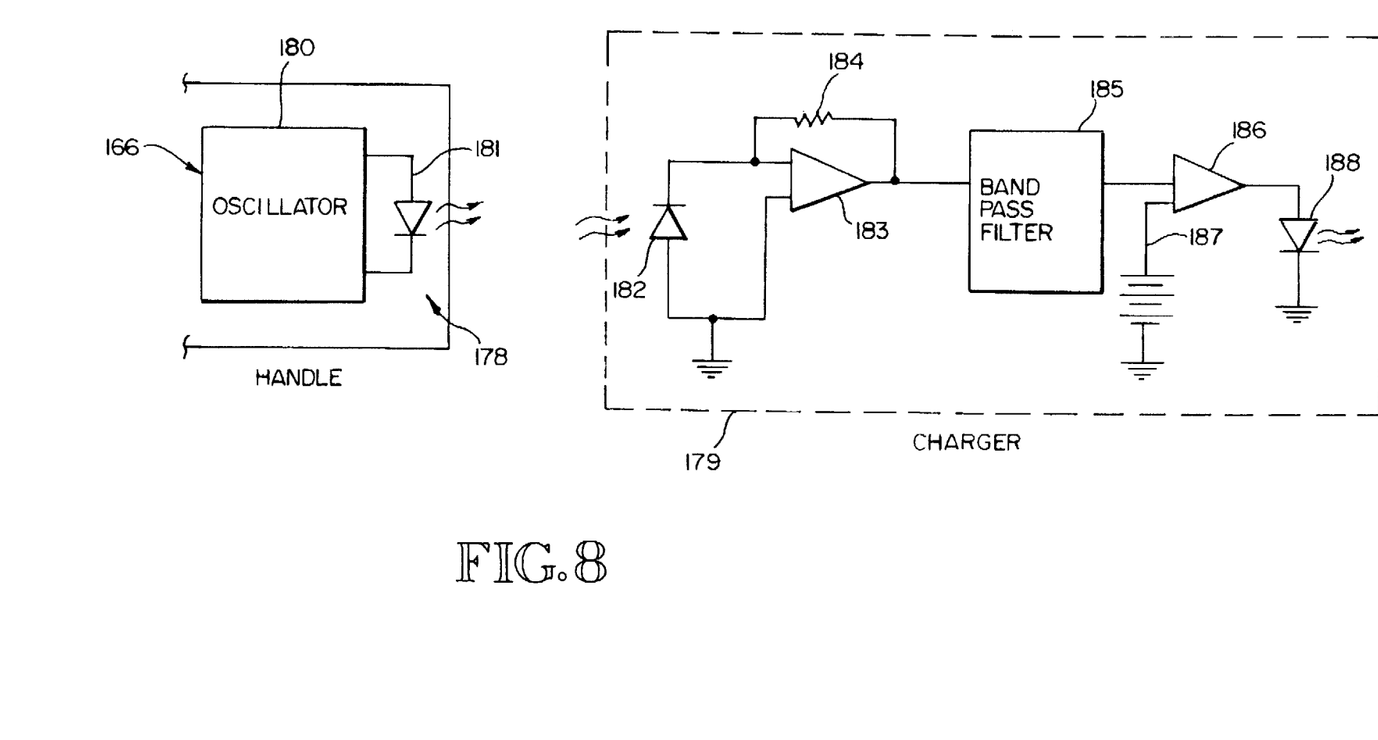
FIG. 8 is a block diagram of an embodiment using a remote visual indicator.

FIG. 8 shows a practical implementation of such an arrangement. Circuit 178 is responsive to overload alarm signal 166, using oscillator 180 to supply a modulated drive to an infrared diode 181, placed so that it is generally capable of transmitting a signal into the room; for example, at the distal end of the handle from the bristles. This signal is then received by a detector circuit 179 placed in the charger, and powered by it. Sufficient coupling between the handle and the charger can be accomplished with relatively low power levels in typical use within a bathroom. The modulation permits suppressing the effects of non-modulated background light; any frequency can be used, typically in the range of 1 kHz–10 kHz, except that harmonics of the line frequency are undesirable. The detector circuit 179 includes a photodetector such as a silicon photodiode 182, followed by a transconductance amplifier comprising an amplifier 183 and feedback resistor 184. The amplified signal is then processed by a filter which is sensitive to the modulated light from LED 181, such as a band pass filter 185 centered at the modulation frequency. The filtered signal is then compared by a comparator 186 with a reference signal 187, and if the filtered signal exceeds the response, a visual indicator is activated, such as LED 188.

The visual indicator can also be used not only to indicate excessive loading but also insufficient loading. For example, the visual indicator could be a two color LED, such as red and green. The LED illumination pattern would be as follows: (1) if the load is less than the minimum threshold, neither LED is on; (2) if the load is above the minimum threshold and below the maximum threshold, only the green LED is on; (3) if the load is above the maximum threshold, only the red LED is on. In the preferred embodiment, the minimum threshold is in a range of 10–30 grams, and the maximum threshold is in a range of 90–150 grams, for a nominal brushing force of 60 grams.

An advantage of this arrangement is that it supplies positive reinforcement to the user, including providing feedback if too little loading is being applied. This three state (in effect) visual indicator can be implemented with two thresholds, two comparators, and two LEDs. The remote indicator arrangement with the LEDs in the charger base can be implemented using multiple modulating frequencies and corresponding band pass filters. Two frequencies and filters can be used to communicate the two LED-on condition with no LED being on when there is not a sufficient amplitude of detectable signal to exceed either threshold.

Figure 6:
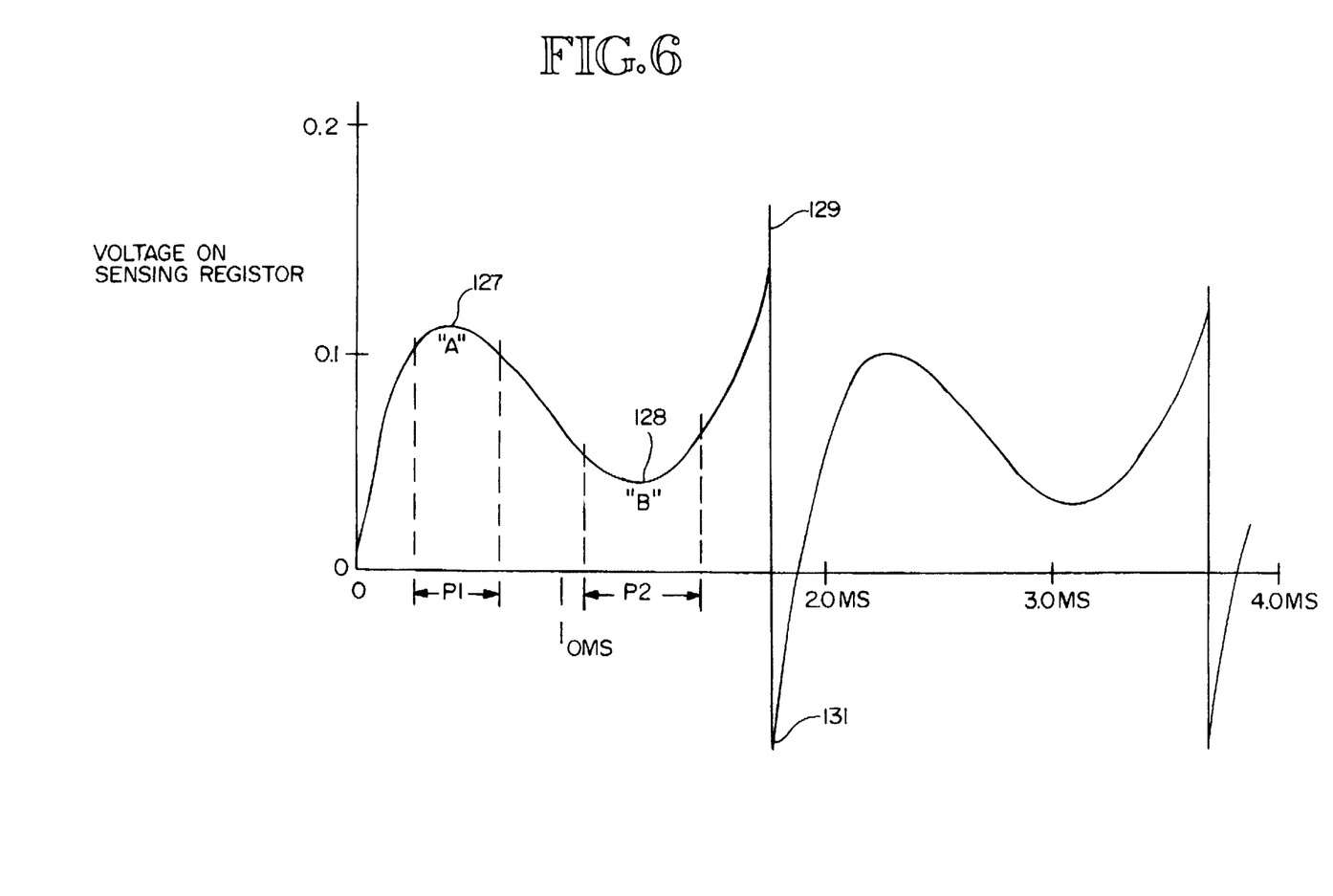
FIG. 6 is a diagram of a waveform representative of the voltages that appear across the power coils of the toothbrush of FIG. 1.

FIG. 6 represents the voltage waveform that appears across sensor resistor 46 during one complete energization cycle of transformer 22. This waveform has two generally similar sinusoidal sections, each representative of a separate biasing of transistors 104 and 106 that occurs during a single energization cycle of the drive assembly 18. As seen by reference to the first sinusoidal section, each sinusoidal section has associated therewith a peak voltage referred to as A-region 127, and a negative peak voltage identified as B-region 128. In between each sinusoidal section of the voltage profile is a relatively sharp positive voltage spike 129 and negative voltage spike 131.

Figure 7:
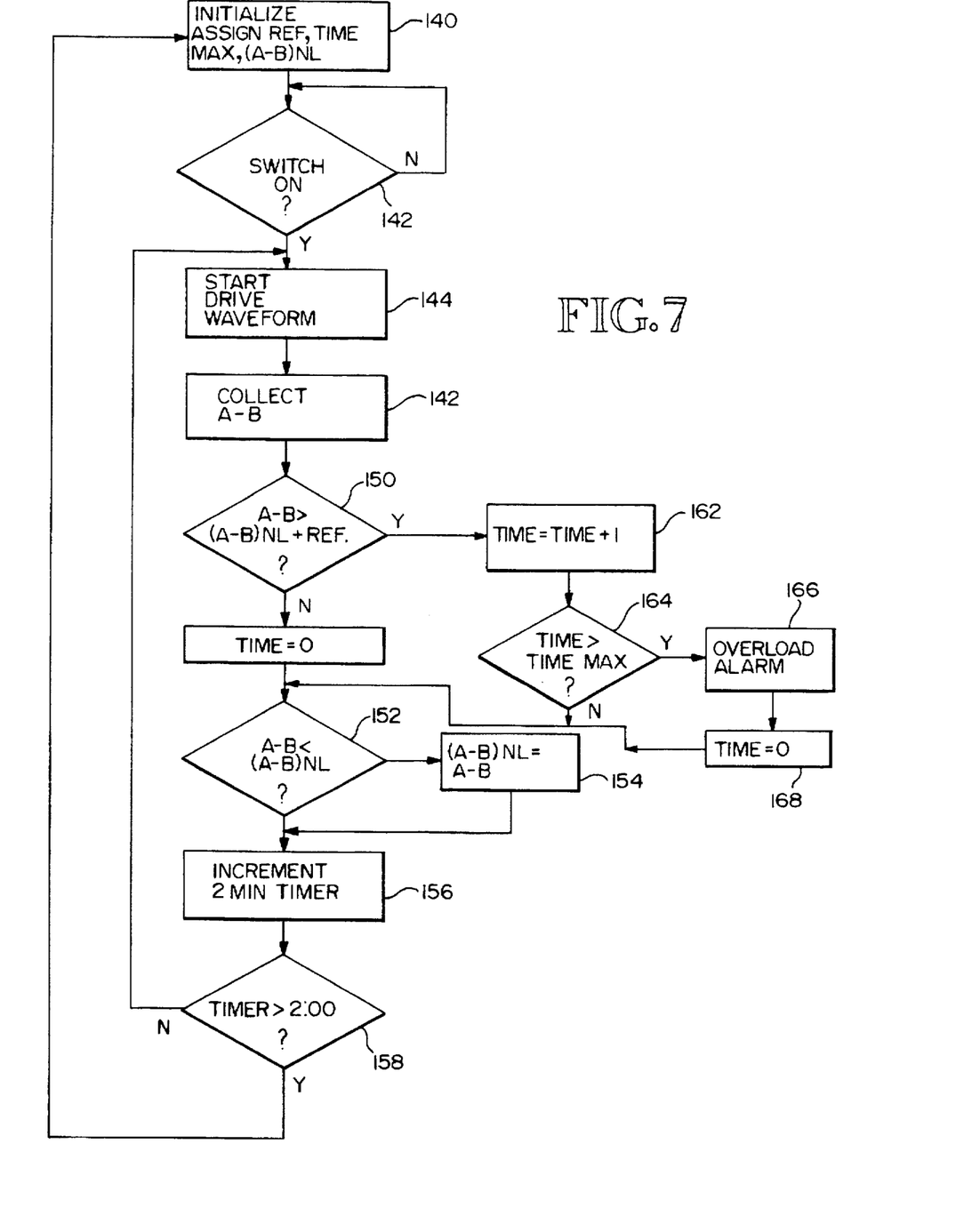
FIG. 7 is a block diagram of the sequence of steps executed by the processor control unit of FIG. 5 for evaluating the load applied to a toothbrush.

FIG. 7 is a flow chart of the process steps executed by the microprocessor 102 as it monitors the load imposed on brushhead 16 and controls the energization of the drive assembly 18. Microprocessor 102 normally is in a quiescent state where it periodically checks to determine if the ON signal has been asserted (block 142). The unit is initialized (block 140) with reference (REF) and time max values being assigned, as well as an initial A-B no-load $(A-B)_{NL}$ value (FIG. 6 shows A and B representative values) which is higher than it could actually ever be. Once the switch on signal is recognized, microprocessor 102 initializes the drive waveforms, as shown at block 144.

Once the microprocessor 102 starts the drive signals, it begins to periodically sample and digitize the load signal that develops across sensor resistor 46. This need not necessarily be done for every drive waveform. In some preferred embodiments of the invention, the voltage across sensing resistor 46 is sampled at a frequency between 10 kHz and 200 kHz and, in still more preferred versions of the invention, at a rate of between approximately 50 kHz and 100 kHz. The digitized load signals are analyzed to find the A region positive peak voltage and B region negative peak voltage so that the A-B peak-to-peak voltage can then be determined, as shown at block 146.

In one implementation of this invention, the A region positive peak voltage is determined by only monitoring the signals during a window in which the voltage signal is expected to rise to its maximum level. The peak voltage is determined by comparing the most recently digitized load signal with the highest peak value previously determined. If the most recent signal is greater in magnitude than the previously stored peak, the most recent digitized signal is stored for the peak. The B region negative peak is similarly determined by initially analyzing the voltage level signals in a time period in which the negative peak is expected. Then, the lowest voltage level measured during that window is stored as the negative peak signal.

Alternatively, the A and B positive and negative peak voltages are determined by integrating the sampled loads throughout the time periods in which they are measured. In this method of analysis, the positive peak voltage is determined based upon finding the particular fraction of time in which the greatest area of integration was present. The negative peak voltage is determined by finding the window of time in which the least area of integration is found.

Microprocessor 102 calculates an initial peak-to-peak voltage level A-B, which is compared to the initial threshold value, which is $(A-B)_{NL}$ plus the selected reference value REF to determine if, upon the actuation of the drive assembly 18, an excessive load has already been placed on the brushhead 14. Such loading may occur if the individual using the toothbrush 10 initially places the brushhead against his/her teeth with an excessive amount of force prior to actuating the drive assembly 18. Typically, however, the answer is no. The step is shown at block 150. The value A-B is then compared against the initial (large) $(A-B)_{NL}$ value, as shown at block 152. If A-B is less than $(A-B)_{NL}$, which occurs when the unit is first turned on, the stored value of $(A-B)_{NL}$ is changed to the initial A-B value (block 154). If A-B is not less than $(A-B)_{NL}$, then $(A-B)_{NL}$ remains the same. The two-minute timer is then incremented at 156 and compared with the maximum value of two minutes at 158. If the elapsed time is less than two minutes, then the drive waveforms are continued (block 144) and the next A-B value is obtained.

In the event the A-B value exceeds $(A-B)_{NL}$+ REF, microprocessor 102 initiates an excess load monitoring sequence. In the embodiment shown, A-B must exceed $(A-B)_{NL}$+ REF for a fixed number of cycles, e.g. 25 cycles, or a comparable time period (10 msec). The comparison is made repeatedly, in block 150.

If the A-B value remains above $(A-B)_{NL}$+ REF, time is accumulated, as shown by block 162, and this accumulated time is then checked against the max time, at block 164. If the comparison reveals that the excess loading has been for a time less than the maximum time, microprocessor 102 continues to initiate the drive waveforms, calculate the A-B signals, and compare the A-B values with $(A-B)_{NL}$+ REF.

If the time comparison reveals that the interval of excess loading is greater than the maximum period, microprocessor 102 then sends a signal to an alarm, as shown at block 166. The interrupt, frequency doubling lamp illumination or other excess loading indication is then produced. The time accumulator is then set back to zero, at block 168. It should be noted that a certain tolerance could be built into the time sequence, so that some percentage, e.g. 80%, of positive comparisons are necessary, instead of 100%, over the specified time, to produce the excess pressure indication.

The embodiment of FIG. 5 provides a convenient means for both energizing an electric toothbrush drive assembly 18, monitoring the load applied to the brushhead, and then taking appropriate action in the event the toothbrush is excessively loaded. As with the previous embodiments of the invention, the embodiment of FIG. 5 does not require any moving parts that need to be built into the toothbrush 10.

Microprocessor 102 constantly monitors the signal across the sensing resistor 46 to determine if the no-load current drawn by the assembly changes. In the event it does change, microprocessor 102 recalculates the adaptive threshold value as needed. The constant updating of the adaptive threshold value ensures that the current load imposed on the toothbrush will always be compared to a threshold value that accurately reflects the maximum load that should be imposed on the toothbrush at any given instant. Thus, the adaptive threshold value will properly be set throughout both an individual brushing cycle and the lifetime of the toothbrush.

Still another feature of the load sensing assembly embodiment of FIG. 5 is that microprocessor 102 does not automatically interrupt the drive signals and/or actuate the alarm at the first instance of brushhead overloading. Instead, microprocessor 102 continues to monitor the load drawn by the drive assembly in order to evaluate if the excess loading is merely a minor, momentary occurrence or loading that is occurring over a sustained period of time. If the latter situation occurs, and there is continual overloading, only then does microprocessor 102 initiate the excess loading indicator. If, on the other hand, loading was just a momentary occurrence, such as may happen if someone for a moment bears down too hard against the toothbrush, the microprocessor will treat the loading as merely a spike event and will continue to energize the drive assembly 18. In this manner, the excess loading indication, when it occurs, is meaningful.

It should be recognized that the foregoing descriptions of the various embodiments of this invention are for the purpose of illustration only and are not intended to limit the scope of the claimed invention. Initially, it should be recognized that while in the description the adaptive load sensor assembly of this invention is described for use with toothbrushes that operate in the sonic range, that it can, of course, be incorporated in toothbrushes that operate at frequencies different from those that have been described.

It should be noted that signals other than (A-B) can be used successfully, as long as they are monotonic in the region of interest. Other useable signals include: A as defined above; or the elapsed time between the initiation of the driving waveform and the occurrence of signal B; or the average of the current; or the voltage across the secondary coil 108. In addition, the drive waveforms shown in FIG. 6 can be operated with a duty cycle of less than 100% (i.e. neither transistor 104 or 106 may be conducting during some part of the waveform). In the case of reduced duty cycle (e.g. 50%), signal A can be used directly instead of (A-B). These other signals may provide greater sensitivity to the load condition being detected.

Similarly, it should be recognized that the circuits forming this adaptive load sensor assembly may be different than those described. For example, it should be clear that it would be readily possible to construct both analog and digital versions of this invention that initially only assert an alarm signal when the brushhead 16 is overloaded, and then only if the brushhead remains in an overloaded condition, would they deenergize the drive assembly 18. The advantage of such construction is that the initial assertion of the alarm would give an individual a chance to ease off on the applied pressure so as to eliminate the need to have to deactivate the drive assembly 18.

With regard to the analog circuit forming the adaptive load sensor assembly, in some versions of this embodiment of the invention, the adaptive threshold signal may be established out of a different set of signals than those that have been described. For instance, in some versions of the invention it may be desirable to provide an adaptive threshold signal that represents the difference between the load signal and a reference signal. Alternatively, it may sometimes be desirable to base the adaptive threshold signal on a stored positive peak of the load signal. Furthermore, in some versions of the invention it may be possible to eliminate the sensor resistor and substitute other circuitry capable of producing a load signal. For instance, depending on the type of energizing signal applied to the drive assembly, in some versions of the invention a frequency counter may be employed to generate a signal that can be used as a load signal representative of the current drawn by the drive assembly.

Similarly, it should also be recognized that some analog and digital versions of the invention may include components different from what have been described above. For example, some versions of the invention may use an analog circuit to capture the load signal and a separate digital circuit to compare the captured signals to the threshold signal.

With regard to the digital versions of this invention, it should be noted that the disclosed microprocessor merely exemplifies one type of processor unit that can be employed to perform the required digital signal processing. In other versions of the invention, discrete analog-to-digital units and programmable logic arrays may be used to ensure that the requisite signal analysis is performed and the desired control signals are asserted.

Moreover, processing steps different from what have been described may be employed in order to monitor the loading of the brushhead 16 and react to any overloading. For example, instead of comparing the load signals to threshold values in order to determine if a toothbrush is overloaded, microprocessor 102 may make such evaluations by determining if the load signal has undergone an excessive rise in a short period of time. Still in other versions of the invention, microprocessor 102 may be set to recognize a number of signal states as being indicative of an excessive loading condition in which action needs to be taken. For example, microprocessor 102 can evaluate either a load signal rise over a short period of time or a load signal rise above a specific threshold level as being indicative of an excess loading state.

A median filter may also be used to minimize effects of short duration load spikes. In digital implementations, low pass filter 72 can be realized with an "infinite impulse response" filter equivalent. Another example is a "finite impulse response" filter, responsive only to a finite length of time of recent history of loading.

Accordingly, it is the object of the appended claims to cover all such variations and modifications as coming within the true spirit and scope of the invention.

We claim:

1. A toothbrush comprising:
   a brushhead including a set of bristles attached thereto;
   a drive assembly connected to said brushhead so as to cause selective movement of said brushhead;
   an energizing circuit connected to said drive assembly for selectively applying a drive signal to said drive assembly so as to actuate said drive assembly, wherein the drive assembly signal varies in accordance with variations in a load on said drive assembly;
   a load sensing assembly for producing a load signal representative of said drive signal, said load sensing assembly being adapted to compare said load signal to a threshold value, and to generate an alarm signal when the load signal/threshold value comparison indicates said brushhead is subjected to a predetermined excessive load, wherein said threshold value is initially set to a preselected load value plus a reference value, prior to the drive assembly being actuated, wherein load value is representative of a no-load condition for the brushhead and wherein the load value and hence the threshold value decrease during a brushing operation as the load value decreases to the smallest amount thereof sensed during each brushing operation, the load value remaining at the smallest load value sensed for the remainder of each brushing operation; and
   an alarm circuit connected to said load sensing assembly and responsive to said alarm signal, said alarm circuit being constructed to generate a warning indicative of the brushhead overloading.

2. The toothbrush of claim 1, wherein said alarm circuit includes a switch connected between said drive assembly and said energizing circuit, for selectively deenergizing said drive assembly when said alarm signal is asserted.

3. The toothbrush of claim 2, wherein said alarm circuit includes an audible alarm unit, said audible alarm unit being configured to generate an audible signal when said alarm signal is asserted.

4. The toothbrush of claim 3, wherein said alarm circuit is configured to deenergize said drive assembly simultaneously with said generation of said audible alarm.

5. The toothbrush of claim 1, wherein said alarm circuit includes an audible alarm unit, said audible alarm unit being configured to generate an audible signal when said alarm signal is asserted.

6. The toothbrush of claim 1, wherein said load sensing assembly includes a comparator to which said load signal and said threshold signal are applied, said comparator being configured to generate said alarm signal when said load signal and said threshold signal have a particular, preselected relationship.

7. The toothbrush of claim 6, wherein said comparator is configured to assert said alarm signal when said load signal is greater than said threshold signal.

8. The toothbrush of claim 6, wherein said load sensor assembly further includes a sample-and-hold circuit for buffering a signal representative of said load signal and an adaptive threshold signal generator, said adaptive threshold signal generator being configured to convert said buffered load signal into an adaptive threshold signal, wherein said adaptive threshold signal is said threshold signal applied to said comparator.

9. The toothbrush of claim 8, wherein said adaptive threshold circuit includes a summing unit for combining said buffered load signal to a reference signal so as to produce said adaptive threshold signal.

10. The toothbrush of claim 1, wherein said pressure sensor assembly includes a digital signal processing unit, said digital signal processing unit being adapted to compare said load signal to said threshold signal, wherein when said load signal and said threshold signal have a preselected relationship, said digital signal processing unit asserts said alarm signal.

11. The toothbrush of claim 10, wherein said digital signal processing unit is connected to said power supply and said drive assembly for controlling said energization of said drive assembly and said digital signal processing unit is further configured to selectively deenergize said drive assembly when said load signal and said threshold signal have a preselected relationship.

12. The toothbrush of claim 1, wherein the load signal is representative of the current drawn by said load assembly.

13. The toothbrush of claim 1, wherein the initial threshold value is in the range of 90–150 grams.

14. The toothbrush of claim 13, wherein the brushhead in operation has a bristle tip velocity of at least 1.5 meters per second.

15. The toothbrush of claim 13, wherein the brushhead in operation has a bristle tip amplitude, said bristle tip amplitude being in the range of one millimeter to six millimeters.

16. The toothbrush of claim 13, wherein the brushhead in operation has a frequency of vibration, said frequency of vibration being in the range of 200 Hz–500 Hz.

17. The toothbrush of claim 13, wherein the brushhead in operation has a bristle tip velocity of at least 1.5 meters per second, a bristle tip amplitude in the range of 1 millimeter to 6 millimeters and a frequency of vibration in the range of 200 Hz–500 Hz.

18. The toothbrush of claim 1, including a second threshold value indicative of insufficient loading of the brushhead.

19. The toothbrush of claim 18 wherein the second threshold value is in the range of 10–30 grams.

20. The toothbrush of claim 18, wherein the alarm circuit includes a first visual indicator indicating that the overloading threshold has been exceeded and a second visual indicator indicating that the second threshold value has not been reached.

21. The toothbrush of claim 20, wherein the first visual indicator is on when the overloading threshold has been exceeded, wherein the second visual indicator is on when the second threshold has been reached but the overloading threshold has not been exceeded, and wherein neither visual indicator is on when the second threshold has not been exceeded.

22. The toothbrush of claim 18, wherein the first and second visual indicators are two different colors.

23. The toothbrush of claim 1, wherein the alarm current includes a visual indicator remote from the toothbrush indicating that the overloading threshold has been exceeded.

24. The toothbrush of claim 23, including means for optically transmitting an energizing signal to said remote visual indicator.

25. The toothbrush of claim 24, wherein said optical transmission means includes a modulated infrared LED, which in operation transmits load condition data to the remote visual indicator.

26. The toothbrush of claim 24, including a charger assembly for said energizing circuit in which the toothbrush is positioned when not in use and wherein said remote visual indicator is located in the charger assembly.

27. The toothbrush of claim 1, wherein the warning occurs for only a relatively short, preselected length of time.

28. The toothbrush of claim 1, wherein the load signal must exceed the threshold value for a pre-selected period of time before the warning occurs, the pre-selected period of time being approximately at least 10 milliseconds.

* * * * *